US008481047B2

(12) United States Patent
Senga et al.

(10) Patent No.: US 8,481,047 B2
(45) Date of Patent: Jul. 9, 2013

(54) MALIGNANT TUMOR-INHIBITING PREPARATION COMPRISING DES A FIBRIN

(75) Inventors: Hirobumi Senga, Tokyo (JP); Caixia Li, Beijing (CN); Yongling Wan, Beijing (CN); Lishui Chang, Beijing (CN)

(73) Assignee: Tobishi Pharmaceutical Co., Ltd., Chiyoda, Ku, Tokyo (JP)

( * ) Notice: Subject to any disclaimer, the term of this patent is extended or adjusted under 35 U.S.C. 154(b) by 1073 days.

(21) Appl. No.: 11/818,783

(22) Filed: Jun. 15, 2007

(65) Prior Publication Data
US 2009/0018062 A1 Jan. 15, 2009

Related U.S. Application Data

(63) Continuation of application No. 11/314,443, filed on Dec. 21, 2005, now abandoned.

(51) Int. Cl.
*A61K 39/385* (2006.01)
(52) U.S. Cl.
USPC ........................................................ 424/193.1
(58) Field of Classification Search
None
See application file for complete search history.

(56) References Cited

U.S. PATENT DOCUMENTS

| 4,957,903 | A | 9/1990 | Ranby |
| 6,682,520 | B2 | 1/2004 | Ingenito |
| 2002/0131935 | A1* | 9/2002 | Fisher et al. ................ 424/1.69 |

FOREIGN PATENT DOCUMENTS

| JP | 10-236984 | 9/1998 |
| WO | WO03/045897 | 11/2002 |

OTHER PUBLICATIONS

Berger et al (Breast Cancer Research and Treatment, 2001, 67:9-14).*
Medl et al (Anticancer Res. 1995, 15(6b):abstract).*
Takagi et al (Gan to Kagaku Ryoho, 2001, 28(11):abstract).*
Isarangkura et al (J. Med. Assoc. Thai., 1999, 82 Suppl 1:abstract).*
Dascombe et al (Thromb Haemost, Aug. 1997, 78(2):abstract).*
Lacroix et al (J Neurosurg, Aug. 2001, 95(2):abstract).*
Itoh et al (Eur Heart J., 1991, 12(2): abstract).*
Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042.).*
Oku et al (Biol. Pharm. Bull., 1997, 843-849).*
Caltagrone et al (Int. J. Cancer, 2000, 87: 595-600).*
Fujii et al (Oncology Research, 1996, 8(9): 333-342).*
Oku et al., Antimetastatic and Antitumor Effect of a Recombinant Human Tissue Inhibitor of Metalloproteinases-2 in Murine Melanoma Models, pp. 843-849, Biol. Pharm. Bull., vol. 20, No. 8, Aug. 1997 Pharmaceutical Society of Japan.

Caltagirone et al., Flavonoids Apigenin and Quercetin Inhibit Melanoma Growth and Metastatic Potential, pp. 595-600, Int. J. Cancer, vol. 87, 2000 Wiley-Liss, Inc.
Fujii et al., Inhibition of Tumor Invasion and Metastasis by Peptidic Mimetics of Arg-Gly ASP(RGD) Derived From the Cell Recognition Site of Fibronectin, pp. 333-342, Oncology Research, vol. 8, No. 9, 1996Elsevier Science, Inc., PII S0965-0407(96)00164-1.
Supplementary European Search Report for related European patent application, Aug. 31, 2009.
Donati et al., "Growth and metastasis of the Lewis lung carcinoma in mice defibrinated with batroxobin" European Journal of Cancer vol. 14, pp. 343-347 (1965).
Chmielewska et al., "Effect of defibrination with batroxobin on growth and metastasis of JW sarcoma in mice" European Journal of Cancer vol. 16 Jan. 1, 1980.
Ivarsson, "Pulmonary metastasis formation after trauma" Acta Chirurgica Scandinavica. Supplementum, Almquist and Wiksell Periodical Co., Stockholm, SE vol. 452 Jan. 1, 1976.
Shibuya et al., "Antimetastatic Effect of Defibrinogenation with batroxobin depends on the natural killer activity of host in mice" Journal of Cancer Research and Clinical Oncology, 116:168-172 (1990).
Hilgard et al., "Anticoagulants in the Treatment of Cancer" European Journal of Cancer vol. 12, pp. 755-762 (1976).
Meh et al., "Sequence of release of fibrinopeptide A from fibrinogen molecules by thrombin or Atroxin" Journal of Laboratory and Clinical Medicine, Mosby, Inc. US, vol. 125 No. 3 Jan. 1, 1995.
Biggerstaff et al., "Soluble fibrin augmens platelet/tumor cell adherence in vitro and in vivi, and enhances experimental metastasis" Clinical & Experimental Metastasis 17: 723-730 1999.
Dehn et al., Clinical Cancer Research, vol. 10, pp. 3417-3155 (2004).
Wang et al., Cancer Research, 63, pp. 7861-7869 (2003).
Official Action for related Chinese Patent Application No. 200580020971.1 with translation, 2009.
Suenson et al. *The Course and Prerequisites of Lys-plasminogen Formation during Fibrinolysis.* Biochemistry 1988, 27, 2435-2443.
Article entitled "The inhibitory effect of batroxobin against the lung metastasis of the B16-F10 melanoma cells implanted in the mice in relation to the activity of the NK cell," (Author: Shigeto Kawachi) (Journal of Nippon Medical School, Dated 1988; 55; pp. 201-208).
Article entitled "Effect of Defibrination with Batroxobin on Growth and Metastasis of JW Sarcoma in Mice," (Authors: J. Chmielewska, A. Poggi, P. Janik, Z.S. Latallo, M.B. Donati) (Eurp J. Cancer, vol. 16, pp. 919-923, Pergamon Press Ltd., Dated 1980, printed in Great Britain).
Article entitled "Studies on Fibrinolysis Induced after Administration of Batroxobin—Especially on the Crosslinkage of $\alpha^2$ Plasmin-inhibitor to Des A Fibrin Polymer," (Author: T. Yamada) (Journal of Tokyo Medical College, Dated 1986, 44; pp. 1067-1077).
Article entitled "Fibrinogen Assembly, Secretion, and Deposition into Extracellular Matrix by MCF-7 Human Breast Carcinoma Cells," (Authors: B.J. Rybarczyk, P.J. Simpson-Haidaris) (Cancer Research 60, Dated Apr. 1, 2000, pp. 2033-2039).

(Continued)

*Primary Examiner* — Sean Aeder
(74) *Attorney, Agent, or Firm* — Husch Blackwell LLP

(57) ABSTRACT

A malignant tumor-inhibiting preparation is provided which comprises Des A fibrin and therefore can inhibit the spreading and migration of malignant tumor cells and thereby can inhibit the malignant tumors.

3 Claims, 9 Drawing Sheets

OTHER PUBLICATIONS

Article entitled "Tumors and Fibrinogen, (The Role of Fibrinogen as an Extracellular Matrix Protein)," (Authors: P.J. Simpson-Haidaris, B. Rybarczyk) (Annals New York Academy of Sciences, Dated 2001; 936; pp. 406-425.

Article entitled "Fibrinogen is an important determinant of the metastatic potential of circulating tumor cells," (Authors: J.S. Palumbo, K.W. Kombrinck A.F. Drew, T.S. Grimes, J.H. Kiser, J.L. Degen, T.H. Bugge) (Blood, Dated Nov. 15, 2000, vol. 96, No. 10; pp. 3302-3309).

Article entitled "Soluble fibrin augments platelet/tumor cell adherence in vitro and in vivo, and enhances experimental metastasis," (Authors: J.P. Biggerstaff, N. Seth, A. Amirkhosravi, M. Amaya, S. Fogarty, T.V. Meyer, F. Siddiqui, J.L. Francis) (Clinical & Experimental Metastasis 17; Dated 1999, pp. 723-730).

Article entitled "A two-step fibrinogen-fibrin transition in blood coagulation," (Authors: B. Blombäck, B. Hessel, D. Hogg, L. Therkildsen) (Nature vol. 275, Dated Oct. 12, 1978, pp. 501-505).

Article entitled "Release of Fibrinopeptides by the Slow and Fast Forms of Thrombin," (Authors: A. Vindigni, E. Di Cera) (Biochemistry, Dated 1996; 35; pp. 4417-4426).

Article entitled "Effect of Defibrination by Defibrase on Tumor Growth and Metastasis," (Author: M. Ojiro) (ACTA Hematol, JPN. 44; Dated 1981, pp. 739-743).

Article entitled "Comparison of the Actions of Thrombin and the Thrombin-Like Venom Enzymes Ancrod and Batroxobin," (Author: D.L. Aronson) (Thrombos Haemostas, (Stuttg.), Dated 1976, pp. 9-13).

Article entitled "The Mechanism of Action of a Coagulant Fraction of Malayan Pit Viper Venom, Arvin, and of Reptilase," (Authors: H.C. Kwaan, G.H. Barlow) (Thromb Diaath Haemorrh, Dated 1971; 45 (Suppl); pp. 63-68).

Article entitled "Fibrinogen and Fibrin—Proteins with Complex Roles in Hemostasis and Thrombosis," (Author: B. Blombäck) (Thrombosis Research, vol. 83, No. 1, Dated 1996, pp. 1-75).

Article entitled "Blood Coagulation, Fibrinolysis and Kinin," (Authors: N. Aoki, S. Iwanaga) (Chugai Igaku Co., © $1^{st}$ ed., pp. 59-71) (Abstract enclosed), 1979.

Article entitled "Molecules in focus (Fibrinogen)," (Authos: S Herrick, O. Blanc-Brude, A. Gray, G. Laurent) (The International Journal of Biochemistry & Cell Biology 31, Dated 1999, pp. 741-746).

Article entitled "Solubility of Fibrin Clots Formed by Snake Venoms," (Author: M. Kato) (ACTA Haematol, JPN, 44; Dated 1981, pp. 706-711).

Article entitled "Invasion of interstitial matrix by a novel cell line from primary peritoneal carcinosarcoma, and by established ovarian carcinoma cell lines: role of cell-matrix adhesion molecules, proteinases, and E-cadherin expression," (Authors: R. Kokenyesi, K.P. Murray, A. Benshushan, E.D. Huntely, Ming-Shian Kao) (Gynecologic Oncology 89; Dated 2003, pp. 60-72, © 2003 Elsevier Science (USA), All rights reserved.).

Article entitled "Inhibition of Cell Migration, Spreading, and Focal Adhesions by Tumor Suppressor PTEN," (Authors: M. Tamura, J. Gu, K. Matsumoto, Shin-ichi Aota, R. Parsons, K.M. Yamada) (Science, vol. 280, Dated Jun. 5, 1998, pp. 1614-1617).

E. Suenson, S. Thorsen—The Course and Prerequisites of Lysplasminogen Formation during Fibrinolvsis; *Biochemistry 1988*, 27, 2435-2443.

R. Ian Freshney—A Culture of Animal Cells—A Manual of Basic Technique; Published by Alan R. Liss, Inc., 1983; 4 pp.

T. Gura—Systems for Identifying New Drugs Are Often Faulty; *Science*, vol. 278, Nov. 1997; pp. 1041-1042.

G. Dermer—Another Anniversary for the War on Cancer; *Biotechnology*, vol. 12; Mar. 1994; p. 320.

* cited by examiner

SEQUENCE LISTING

<160> NUMBER OF SEQ ID NOS: 2

<210> SEQ ID NO 1
<211> LENGTH: 16
<212> TYPE: PRT
<213> ORGANISM: human

<400> SEQUENCE: 1

Ala Asp Ser Gly Glu Gly Asp Phe Leu Ala Glu Gly Gly Gly Val Arg
1               5                   10                  15

<210> SEQ ID NO 2
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: AMIDATION

<400> SEQUENCE: 2

Gly Pro Arg Pro
1

MALIGNANT TUMOR-INHIBITING PREPARATION COMPRISING DES A FIBRIN

CROSS-REFERENCE TO RELATED APPLICATIONS

This application claims priority from U.S. Continuation application Ser. No. 11/314,443, filed on Dec. 21, 2005; which is based on PCT Application No. PCT/JP2005/012174 filed Jun. 24, 2005, which claims priority from Japanese patent application No. 2004-213635 filed Jun. 24, 2004.

TECHNICAL FIELD

The present invention relates to a malignant tumor-inhibiting preparation comprising Des A fibrin.

BACKGROUND ART

Malignant tumor therapy is progressing steadily in recent years by improving in successful rate for removal of the primary carcinoma by surgical operations, radiotherapies, or chemotherapies. However, even if a primary carcinoma is completely removed, death frequently occurs due to cancer metastasis.

In particular, melanoma, lung cancer, liver cancer, pancreatic cancer and other malignant tumors with a high malignancy, were difficult to detect in the early stages, so that by the time a malignant tumor is diagnosed, both the primary cancer and the metastatic cancer can be already existed simultaneously, and surgical treatment is impossible in many cases. Also, radiotherapies do not show good result for therapy of these malignant tumors. Moreover, most chemotherapeutic drugs in current clinical use, such as adriamycin, work by directly attacking the malignant tumor cells, but since they simultaneously target normal cells, they have strong side-effects which are a problem for clinical use. Therefore, no revolutionary new drug has emerged in decades. In order to overcome such a situation, it looks forward to the new type drugs for treating malignant tumors.

In this context, many basic studies and clinical studies have suggested a close relationship between malignant tumors and the blood coagulation and fibrinolysis systems, recently. For example, it is known that microcirculatory injury is caused by increased plasma fibrinogen levels, increased blood viscosity, abnormal blood rheology and other abnormalities of the blood coagulation and fibrinolysis systems in malignant tumor patients. It has also been reported that increased plasma fibrinogen levels or secretion of fibrinogen by the malignant tumor cells themselves causes the deposition of fibrinogen or fibrin into the extracellular matrix of the malignant tumor tissues, and these factors have the effect as part of the extracellular matrix to promote proliferation, invasion and metastasis of the malignant tumor cells (see for example *Cancer Research* 60:2033-2039 (2000); *Ann. NY Acad. Sci.* 936:406-425 (2001); and *Blood* 96:3302-3309 (2000)).

Focusing on the aforementioned relationship between malignant tumors and the blood coagulation and fibrinolysis systems, it has been confirmed that when malignant tumor cells are treated with fibrin in vitro, there is an increase effect of fibrin on the experimental metastasis of the malignant tumor cells into the lungs (see for example *Clin. Exp. Metastasis* 17:723-730 (1999)). Fibrin (also called Des AB fibrin or fibrin II) is a substance obtained when thrombin acts on fibrinogen, causing the release of fibrinopeptide A (FPA) and fibrinopeptide B (FPB) from the fibrinogen (see for example *Nature* 275:501-505 (1978) and *Biochemistry* 35:4417-4426 (1996)).

Moreover, focusing on the relationship between plasma fibrinogen concentrations and growth and metastasis of malignant tumors, it has been reported that administration of the thrombin-like enzymes batroxobin and ancrod, which have a defibrinogenating effect, reduces fibrinogen and inhibits malignant tumor growth and metastasis (see for example *Eur. J. Cancer* 16:919-923 (1980); and *Acta Haematol. Jpn.* 44:739-743 (1981)). Batroxobin, a thrombin-like serine protease produced from the venom of the snake Bothrops atrox moojeni, is a glycoprotein enzyme which releases only FPA from fibrinogen to produce Des A fibrin (also called fibrin I) (see for example *Thromb. Haemost.* 36:9-13 (1976) and *Thromb. Diath. Haemorrh.* 45(Suppl.):63-68 (1971)).

Based on the assumption that fibrinogen functions as a barrier to protect malignant tumor cells from the attacks of the immune system, the technologies disclosed in above-mentioned references, attempted to inhibit growth and metastasis of malignant tumors by reducing fibrinogen levels with thrombin-like enzymes, thus making it easier for the immune system to attack the malignant tumor cells.

On the other hand, it is also known that the malignant tumor cell has characteristics of spreading and migration. "Spreading" of malignant tumor cells in this case, means that the round tumor cells form pseudopodia in response to some signal, and this is a biological behavior of tumor cells, which becomes the basis of tumor growth, invasion and metastasis.

Moreover, "migration" of malignant tumor cells means that the tumor cells move from their original locations through repeated bindings and dissociations between ligands and cell adhesion molecules in the cell membrane in response to some signal, and this is also a biological behavior which becomes the basis of tumor invasion and metastasis.

Therefore, by inhibiting the spreading and migration of malignant tumor cells, it is possible to inhibit tumor invasion and metastasis and thus inhibit malignant tumors.

However, there have been no reports on a preparation that can inhibit the spreading and migration of malignant tumor cells in order to effectively inhibit malignant tumor.

Furthermore, there have been no reports on the relationship between Des A fibrin (fibrinogen degradation product) and the spreading and migration of malignant tumor cells.

DISCLOSURE OF THE INVENTION

Consequently, it is an object of the present invention to provide a malignant tumor-inhibiting preparation comprising a novel active ingredient, which is a malignant tumor-inhibiting preparation.

To resolve the aforementioned issues, the inventors considered that Des A fibrin might have a different effect than fibrin on malignant tumor cells, and after exhaustive researches into the effect of Des A fibrin on malignant tumor cell spreading and migration, they discovered that Des A fibrin acts to inhibit the spreading and migration of malignant tumor cells. The present invention is based on this finding.

That is, the present invention relates to a malignant tumor-inhibiting preparation comprising Des A fibrin.

BEST MODE FOR CARRYING OUT THE INVENTION

Figure 1:
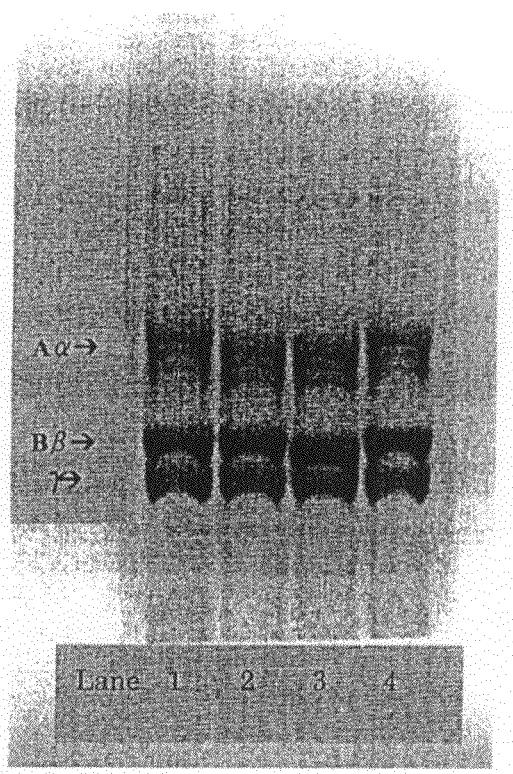
FIG. 1 is a photograph showing electrophoretogram of fibrinogen, Des A fibrin and fibrin.

The present invention is explained in detail below.

The malignant tumor-inhibiting preparation of the present invention comprises Des A fibrin as an active ingredient.

Des A fibrin is a substance obtained by releasing FPA from fibrinogen.

Fibrinogen is a dimeric glycoprotein $(A\alpha B\beta\gamma)_2$ formed by the disulfide linkages of two subunits $(A\alpha B\beta\gamma)$, each consisting of three chains of an $A\alpha$ chain, a $B\beta$ chain and a $\gamma$ chain which are bound by disulfide linkages. Since the $A\alpha$ chain consists of 610 amino acids (68 kDa), the $B\beta$ chain of 461 amino acids (54 kDa), and the $\gamma$ chain of 411 amino acids (48 kDa), the molecular weight of fibrinogen is 340 kDa (see *Thromb. Res.* 83:1-75 (1996) and Blood Coagulation, Fibrinolysis and Kinin, Aoki, A. and Iwanaga, S. (Eds), Chugai Igaku Co., Tokyo, 1979, pp. 59-71). It is also known that while the $B\beta$ chain and $\gamma$ chain have sugar bound thereto, the $A\alpha$ chain does not (see *Int. J. Biochem. & Cell Biol.* 31:741-746 (1999)).

FPA is a peptide corresponding to the 16 amino acids ($NH_2$-Ala-Asp-Ser-Gly-Glu-Gly-Asp-Phe-Leu-Ala-Glu-Gly-Gly-Gly-Val-Arg) (Seq. ID No. 1) at the amino terminal end of the Aa chain of fibrinogen.

Therefore, Des A fibrin is the residue $[(\alpha B\beta\gamma)_2]$ obtained when FPA is released from fibrinogen (see *Thromb. Haemost.* 36:9-13 (1976) and *Thromb. Diath. Haemorrh.* 45 (Suppl.): 63-68 (1971)). Since the molecular weight of FPA is 1,536 Da, the molecular weight of Des A fibrin is calculated to be about 337 kDa.

Thrombin-like enzymes can be used to release FPA from fibrinogen. The thrombin-like enzyme is a kind of serine protease. Those derived from snake venom are commonly used. Specific examples include batroxobin (Tobishi Pharmaceutical Co., Ltd. and Beijing Tobishi Pharmaceutical Co., Ltd., Beijing, China, a subsidiary company of Tobishi Pharmaceutical Co., Ltd.), which is extracted and purified from the venom of Bothrops atrox moojeni, as well as ancrod and other thrombin-like enzymes (such as Crotalase) which are derived from snake venom and the like. These thrombin-like enzymes may be naturally occurring preparations or may be products of genetic recombination.

Des A fibrin can be manufactured for example by the methods described in (1) through (6) below using fibrinogen and a thrombin-like enzyme:

(1) A method in which fibrinogen is made to adhere to the surface of a plastic culture vessel, glass culture vessel, glass slide, stainless steel or an artificial blood vessel of the artificial solid substance EPTFE or the like, and a thrombin-like enzyme is added thereto to manufacture Des A fibrin;

(2) A method in which fibrinogen and a thrombin-like enzyme are added simultaneously to the aforementioned solid substance to manufacture Des A fibrin;

(3) A method in which fibrinogen and a thrombin-like enzyme are reacted in a liquid reaction system in the presence of 0.1 to 15 N of urea and/or an anticoagulation peptide (Gly-Pro-Arg-Pro-amide, GPRP-$NH_2$ (Seq. ID NO. 2)) to prepare Des A fibrin while preventing agglutination between Des A fibrin monomer (*Clin. Exp. Metastasis* 17: 723-730 (1999));

(4) A method in which fibrinogen is bound to a column, and a solution comprising a thrombin-like enzyme is poured in to manufacture Des A fibrin;

(5) A method in which a thrombin-like enzyme is bound to a column, and a solution comprising fibrinogen is poured in to manufacture Des A fibrin; and (6) A method in which a thrombin-like enzyme is administered intravenously, intraperitoneally, subcutaneously, intramuscularly or the like so that it acts on fibrinogen in the body to manufacture Des A fibrin in vivo (see *Acta Haematol. Jpn.* 44:706-711 (1981)).

The fibrinogen and thrombin-like enzyme used to manufacture Des A fibrin in the present invention are themselves known substances, which can be easily obtained commercially or prepared. Des A fibrin itself is also a known substance that can be prepared by the aforementioned methods.

The malignant tumor-inhibiting preparation of the present invention is targeted at malignant tumors. Depending on the tissue's original occurrence, malignant tumors can be generally classified into epithelial malignant tumors and non-epithelial malignant tumors. About 90% of tumors are said to be epithelial tumors. Non-epithelial malignant tumors can be further classified into malignant tumors derived from mesenchymal tissue, malignant tumors derived from neural tissue and malignant tumors derived from undifferentiated cells. Specific examples of each kind of malignant tumor are given below.

Epithelial Malignant Tumors

Adenocarcinomas (carcinomas derived from glandular epithelium, which occur throughout the body including the stomach, intestines, pancreas, trachea, lungs, mammary glands, ovaries, corpus uteri, prostate glands and the like, are supposed to constitute 70 to 80% of human cancers), squamous cell carcinomas (cancers derived from the stratified squamous epithelium and occurring in epithelial tissue of the epidermis, lips, tongue, throat, esophagus, anus, vulva, uterine cervix and the like, and pulmonary squamous epithelial cancers classified as non-small cell lung cancer), basal cell carcinomas (derived from basal cells of the skin and adnexa), transitional cell carcinomas (derived from transitional epithelium, such as bladder cancer), liver cell carcinomas (derived from hepatocytes), renal cell carcinomas (derived from renal epithelium), cholangiocarcinomas (derived from the bile duct) and choriocarcinomas (derived from the placental epithelium)

Non-Epithelial Malignant Tumors
Malignant Tumors Derived from Mesenchymal Tissue Fibrosarcomas (derived from connective tissue and fibrous tissue), liposarcomas (derived from connective tissue and fatty tissue), chondrosarcomas (derived from connective tissue and cartilaginous tissue), osteosarcomas (derived from connective tissue and bone tissue), angiosarcomas (derived from blood vessels), lymphangiosarcomas (derived from lymphoducts), myelogenic leukemia (derived from hemopoietic cells), monocytic leukemia (derived from hemopoietic cells), malignant lymphoma (derived from lymphoid tissue), lymphocytic leukemia (derived from lymphoid tissue), plasmacytoma (multiple myeloma, derived from lymphoid tissue), Hodgkin's cell (derived from lymphoid tissue), leiomyosarcoma (derived from smooth muscle), rhabdomyosarcoma (derived from striated muscle)

Malignant Tumors Derived from Neural Tissue

Neuroblastoma (derived from neuroblasts), medulloblastoma (derived from medulloblasts), malignant astrocytoma (derived from astrocytes), retinoblastoma (derived from retinoblasts), glioblastoma (derived from glioblasts), malignant neurilenoma (derived from Schwann cells), melanoma (derived from neuroectoderm)

Malignant Tumors Derived from Undifferentiated Cells

Malignant teratoma (derived from totipotent cells), nephroblastoma (derived from nephroblasts), hepatoblastoma (derived from hepatoblasts), mixed tumors (derived from various types of cells).

Of these malignant tumors mentioned above, the malignant tumor-inhibiting preparation of the present invention can be highly effective against epithelial malignant tumors, and against non-epithelial malignant tumors derived from neural tissue and mesenchymal tissue, particularly melanoma, breast cancer and fibrosarcoma.

The malignant tumor-inhibiting preparation of the present invention can inhibit tumor invasion and metastasis by inhibiting the spreading and migration of malignant tumor cells, and can thus inhibit malignant tumors.

"Spreading" of malignant tumor cells in this case, means that the round tumor cells form pseudopodia in response to some signal, and this is a biological behavior of tumor cells, which becomes the basis of tumor cell proliferation, invasion and metastasis.

Moreover, the "migration" of malignant tumor cells means that the movement of tumor cells from their original locations through repeated bindings and dissociations between ligands and cell adhesion molecules on the cell membrane in response to some signal, and this is also a biological behavior which becomes the basis of tumor invasion and metastasis.

The malignant tumor-inhibiting preparation of the present invention may comprise Des A fibrin either by itself or in combination with other active substances.

Examples of other active substances include antimetabolites such as fluorouracil, antitumor antibiotics such as adriamycin, alkylating agents such as dacarbazine, plant-derived anticancer drugs such as paclitaxel and the like.

Any formulation in the Japanese Pharmacopoeia General Rules for Preparations can be applied to the formulation of the malignant tumor-inhibiting preparation of the present invention. Examples of the formulation of the malignant tumor-inhibiting preparation of the present invention include injections for direct application inside the body (including suspensions and emulsions); ointments (including fatty ointments, emulsion ointments (creams), water-soluble ointments and the like), inhalants, liquids (including ophthalmic solutions, collunarium and the like), suppositories, patches, poultices, lotions and other external formulations; and internal formulations including tablets (including sugar-, film- and gelatin-coated), liquids, capsules, granules, powders (including grains), pills, syrups, troches and the like. These formulations can be prepared by the methods described in the Japanese Pharmacopoeia General Rules for Preparations.

The malignant tumor-inhibiting preparation of the present invention may also include pharmacologically acceptable solid or liquid carriers or interventional therapy bases. Examples of pharmacologically acceptable solid or liquid carriers include solvents, stabilizers, preservatives, solubilizing agents, emulsifiers, suspending agents, buffering agents, isotonizing agents, coloring agents, bases, thickeners, excipients, lubricants, binding agents, disintegrating agents, coating agents, corrigents and the like.

Specific examples include water, lactose, sucrose, fructose, glucose, mannitol, sorbitol and other sugars and sugar alcohols, crystalline cellulose, methylcellulose, ethylcellulose, hydroxypropylcellulose, low substituted hydroxypropylcellulose, hydroxypropylmethylcellulose, hydroxypropylmethylcellulose phthalate, hydroxypropylmethylcellulose acetate succinate, carmellose, carmellose calcium, carmellose sodium, croscarmellose sodium, carboxymethylethylcellulose, cellulose acetate phthalate and other celluloses and related derivatives, corn starch, wheat starch, rice starch, potato starch, dextrin, pregelatinized starch, partly pregelatinized starch, hydroxypropyl starch, sodium carboxymethyl starch, cyclodextrin, pullulan and other starches and related derivatives, agar, sodium alginate, acacia, gelatin, collagen, shellac, tragacanth, xanthan gum and other natural polymers (seaweeds, plant mucilage, proteins and the like), polyvinylpyrrolidone, aminoalkyl methacrylate copolymer, methacrylic acid copolymer, carboxyvinyl polymer, polyvinyl alcohol, dimethylpolysiloxane and other synthetic polymers, olive oil, cacao butter, carnauba wax, beef tallow, hydrogenated oil, soybean oil, sesame oil, camellia oil, paraffin, liquid paraffin, yellow beeswax, white petrolatum, coconut oil, microcrystalline wax and other oils and fats, stearic acid, aluminum stearate, calcium stearate, magnesium stearate, triethyl citrate, triacetine, medium chain fatty acid triglyceride, hard fat, isopropyl myristate and other fatty acids and derivatives thereof, glycerin, stearyl alcohol, cetanol, propylene glycol, macrogol and other alcohols and polyvalent alcohols, zinc oxide, dibasic calcium phosphate, precipitated calcium carbonate, synthetic aluminum silicate, silicon dioxide anhydride, kaolin, dried aluminum hydroxide gel, synthetic hydrotalcite, titanium oxide, talc, bentonite, magnesium aluminometasilicate, aluminum potassium sulfate, bismuth subgallate, bismuth subsalicylate, calcium lactate, sodium bicarbonate and other inorganic substances and metal salt compounds, sucrose esters of fatty acid, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, lauromacrogol and other surfactants, dyes, perfumes and the like.

Examples of intervention therapy bases include stents, artificial blood vessels and the like.

The amount of Des A fibrin contained in the malignant tumor-inhibiting preparation of the present invention varies depending on the formulation adopted. Case examples include 0.01 to 900 mg per 1 g in the case of a formulation for internal use, 0.01 to 500 mg per 1 ml in the case of an injection or 0.01 to 500 mg per 1 g in the case of a formulation for external use.

The administered dose of the malignant tumor-inhibiting preparation of the present invention varies depending on the patient's weight, disease's property and condition, but is for example 0.1 to 5,000 mg or preferably 100 to 2,500 mg of Des A fibrin per day in the case of an adult.

The present invention is described in detail below using examples, but is not limited by these examples.

Example 1

Preparation and Identification of Des A Fibrin

Des A fibrin was prepared by using a thrombin-like enzyme to release FPA from fibrinogen. Moreover, production of Des A fibrin was identified through a comparison with fibrinogen and fibrin.

(1) Preparation of Des A Fibrin

The thrombin-like enzyme batroxobin (Tobarpin®, Beijing Tobishi Pharmaceutical Co., Ltd., Beijing, China) was added to a phosphate-buffered (PBS) solution of human fibrinogen (F-4883, Sigma, Mo., USA) to make a final reaction solution with fibrinogen concentration of 3.0 mg/ml and batroxobin concentration of 0.5 BU/ml, and incubated for 1 hour at 37° C. in order to prepare Des A fibrin.

(2) Preparation of Fibrin

A PBS solution of thrombin (Sigma, Mo., USA) was added to a PBS solution of human fibrinogen (F-4883, Sigma, Mo., USA) to make a final reaction solution with fibrinogen concentration of 3.0 mg/ml and thrombin concentration of 0.5 U/ml, and incubated for 1 hour at 37° C. in order to prepare fibrin.

(3) Preparation of Fibrinogen

A PBS solution of fibrinogen with a final concentration of 3.0 mg/ml was prepared using human fibrinogen (F-4883, Sigma, Mo., USA) as an untreated control.

(4) Identification of Des A Fibrin Production

The production of Des A fibrin in Process (1) mentioned above was identified by electrophoresis. Specifically, given that fibrinogen is reduced into three-type chains (Aα, Bβ and γ chains) by the following treatment, productions were evaluated by electrophoresis after reduction of Des A fibrin into three-type chains (α, Bβ and γ chains) and reduction of fibrin into three-type chains (α, β γ chains).

The Des A fibrin obtained in Process (1) and the fibrin obtained in Process (2), were washed three times with sterilized isotonic sodium chloride solution, and boiled for 5 to 6 minutes in 0.5 ml of 2% SDS/2% beta-mercaptoethanol/5 M urea solution to break the disulfide bonds, and dissolved.

The fibrinogen obtained in process (3) that was subjected to the same treatment process as above exclusion of the washing process, to break the disulfide bonds, and dissolved by boiling.

Fifty microliter of electrophoretic buffer (4×2% SDS/0.1% bromcresol blue) was added to 150 µl of each sample solution, and 7.5% SDS-PAGE (Pagel®, Atto Corp., Tokyo, Japan) was performed.

The results are shown in FIG. 1 as an electrophoretogram. In FIG. 1, Lane 1 and Lane 4 show fibrinogen, Lane 2 shows Des A fibrin and Lane 3 shows fibrin.

In each lane, the lowest band represents the γ chain, the second band from the bottom represents the Bβ chain, and the third band from the bottom represents the Aα chain.

Evaluating Lane 2 (Des A fibrin) on the basis of Lane 1 and Lane 4 (fibrinogen) as the standard, the position of the third band from the bottom (Aα chain) in Lane 2 is shifted lower (towards lower molecular weight side). This indicates that FPA has been released from the Aα chain of fibrinogen by the action of the thrombin-like enzyme batroxobin. The positions of the other bands are in concordance with those of the fibrinogen. Therefore, it can be understood that in Process (1) FPA was released from fibrinogen and resulting in the production of Des A fibrin.

Evaluating Lane 3 (fibrin) on the basis of Lane 1 and Lane 4 (fibrinogen) as the standard, the positions of the second band from the bottom (Bβ chain) and the third band from the bottom (Aα chain) in Lane 3 are shifted lower (towards lower molecular weight side). These indicate that FPA and FPB have been released from the Aα chain and Bβ chain of fibrinogen by the action of thrombin. Therefore, it can be understood that fibrin was produced in Process (2).

These results mentioned above were in concordance with previously published data (see *Acta Haematol. Jpn.* 44:706-711 (1981)).

Figure 2:
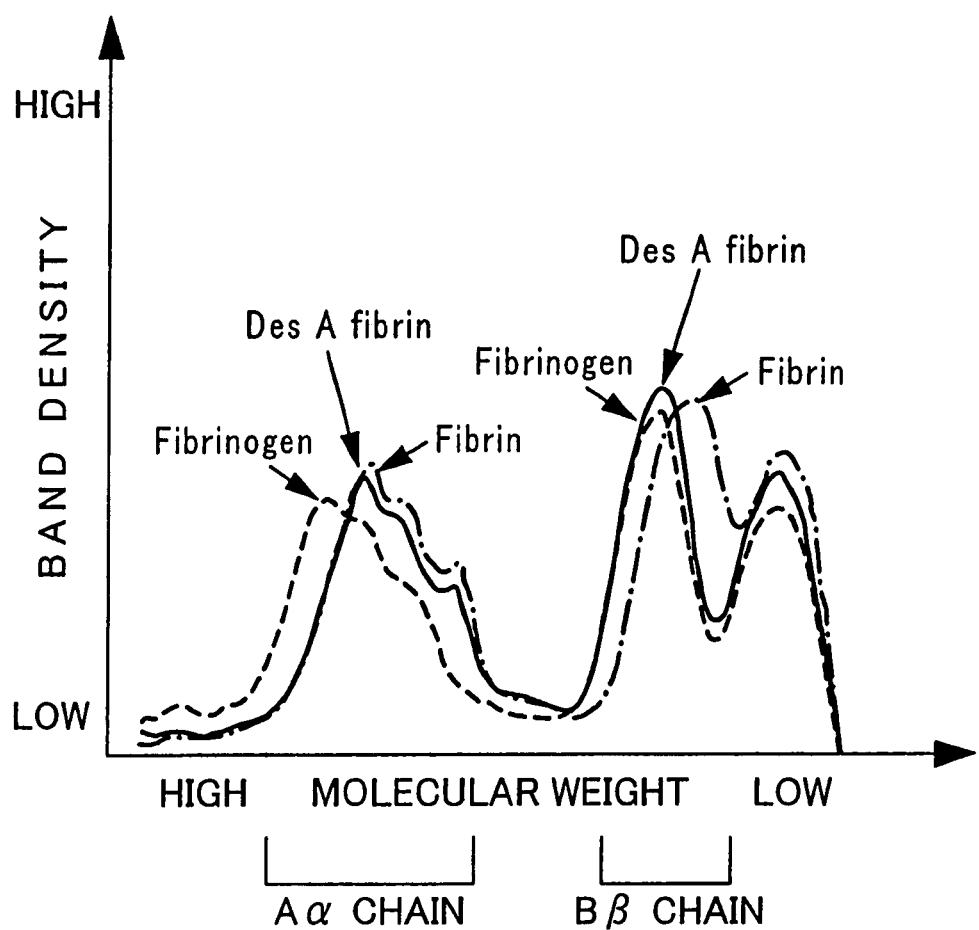
FIG. 2 is a graph showing the electrophoretogram of FIG. 1 quantified by an image analyzing system.

The aforementioned electrophoretogram was quantified by using an image analyzing system (Furi Science & Technology Co., Ltd., Shanghai, China), and represented in FIG. 2.

As for three peaks in FIG. 2, the left peak shows the band density of the Aα chain, the middle peak shows the band density of the Bβ chain, and the right peak shows the band density of the γ chain.

When evaluating the left peak (Aα chain), the peaks of Des A fibrin and fibrin were in concordance with each other, and were shifted towards the lower molecular weight side than the peak of fibrinogen. These indicate that in Des A fibrin and fibrin, FPA has been released from the Aα chain of fibrinogen.

When evaluating the middle peak (Bβ chain), the peaks of fibrinogen and Des A were in concordance with each other, while the peak of fibrin is shifted towards the lower molecular weight side. These indicate that in fibrin, FPB has been released from the Bβ chain of fibrinogen.

As mentioned above, this identifies that the substance produced by the action of batroxobin on fibrinogen (($A\alpha B\beta\gamma)_2$) is Des A fibrin (($\alpha B\beta\gamma)_2$), while the substance produced by the action of thrombin on fibrinogen is fibrin (($\alpha\beta\gamma)_2$).

Example 2

Effect of Des A Fibrin on Spreading of Malignant Tumor Cells

Matrigel® (BD Biosciences, NJ, USA) was utilized to establish an artificial extracellular matrix environment in vitro, and three types of malignant tumor cells (melanoma, breast cancer and fibrosarcoma) were used to evaluate the effect of Des A fibrin on spreading of malignant tumor cells in this environment.

(1) Malignant Tumor Cells Used

B16-BL6 mouse malignant melanoma cells (Academy of Chinese Medical Sciences, Beijing, China) as the melanoma cells were subcultured in RPMI-1640 medium (Gibco, MD, USA) containing 10% fetal bovine serum (FBS, HyClone, Utah, USA), and the cells were used in the present experiment.

MMT060562 mouse breast cancer cells (ATCC, VA, USA) as the breast cancer cells were subcultured in MEM medium (Gibco, MD, USA) containing 10% FBS and 1% nonessential amino acids solution (Non-Essential Amino Acids Solution, Gibco, MD, USA), and the cells were used in the present experiment.

HT-1080 human fibrosarcoma cells (Academy of Chinese Medical Sciences, Beijing, China) as the fibrosarcoma cells were subcultured in MEM medium (Gibco, MD, USA) containing 10% FBS, and the cells were used in the present experiment.

(2) The Method of Measuring Cell Spreading

Two hundred fifty microliter of Matrigel (Matrigel® 7.5 μg/ml, BD Biosciences, NJ, USA) was added to each well of an eight-chamber slide (Nunc, IL, USA), and incubated for 1 hour at room temperature to coat the slide with the Matrigel. Next, the following solutions A through F (0.25 ml) was added to the Matrigel-coated well, respectively.

A: Addition of phosphate-buffered saline (PBS) (solvent control)
B: Addition of fibrinogen (3 mg/ml)
C: Addition of batroxobin (0.5 BU/ml)
D: Addition of thrombin (0.5 U/ml)
E: Addition of Des A fibrin (3 mg/ml fibrinogen and 0.5 BU/ml batroxobin)
F: Addition of fibrin (3 mg/ml fibrinogen and 0.5 U/ml thrombin)

All the solvent used for the above treatment was PBS.

(Here, the BU (batroxobin unit) is a unit indicating the enzymatic activity of batroxobin; with 2 BU being the activity to achieve coagulation in 19.0±0.2 seconds when 0.1 ml of batroxobin solution is added to 0.3 ml of standard human plasma containing citric acid at 37° C.)

In A through D, the components were added to the wells in the indicated final concentration and incubated for 1 hour at room temperature, the liquid was then discarded, and the wells were washed with PBS.

In E and F, the components were added to the wells in the indicated final concentration, and reacted for 60 seconds, and the liquid was discarded before the product (treatment E: Des A fibrin, treatment F: fibrin) could coagulate. This was followed by incubation for 1 hour at room temperature and washing with PBS. In the case of treatment E, Des A fibrin was produced by the action of batroxobin on fibrinogen, while in the case of treatment F fibrin was produced by the action of thrombin on fibrinogen.

Five thousand six hundred of B16-BL6 melanoma cells, suspended in serum-free RPMI-1640 medium, were seeded in each treated well, and the chamber slide was incubated for 2 hours in a $CO_2$ incubator. The number of spreading cells (those having pseudopodia) among about 150 cells adhering to each treated well was counted using a phase contrast microscope, and the percentage of spreading cells was calculated as the spreading rate according to the following formula.

Spreading rate(%)=(number of spreading cells/number of adhering cells)×100

The same procedures were applied to 5,600 MMT060562 breast cancer cells suspended in serum-free MEM medium containing 1% nonessential amino acid solution, and 5,600 HT-1080 fibrosarcoma cells suspended in serum-free MEM medium in place of the 5,600 B16-BL6 melanoma cells suspended in serum-free RPMI-640 medium.

(3) Inhibition of Melanoma Cell Spreading

Figure 3:
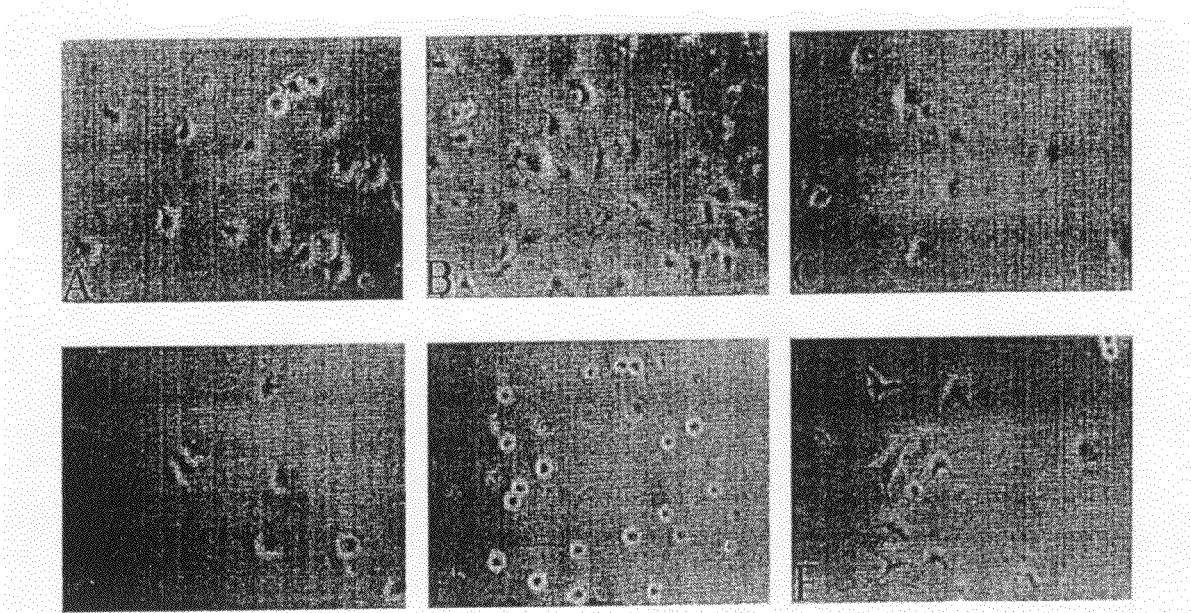
FIG. 3 shows photomicrographs of melanoma cells which were cultured in the PBS (A), fibrinogen (B), batroxobin (C), thrombin (D), Des A fibrin (E) and fibrin (F)-treated wells.
Figure 4:
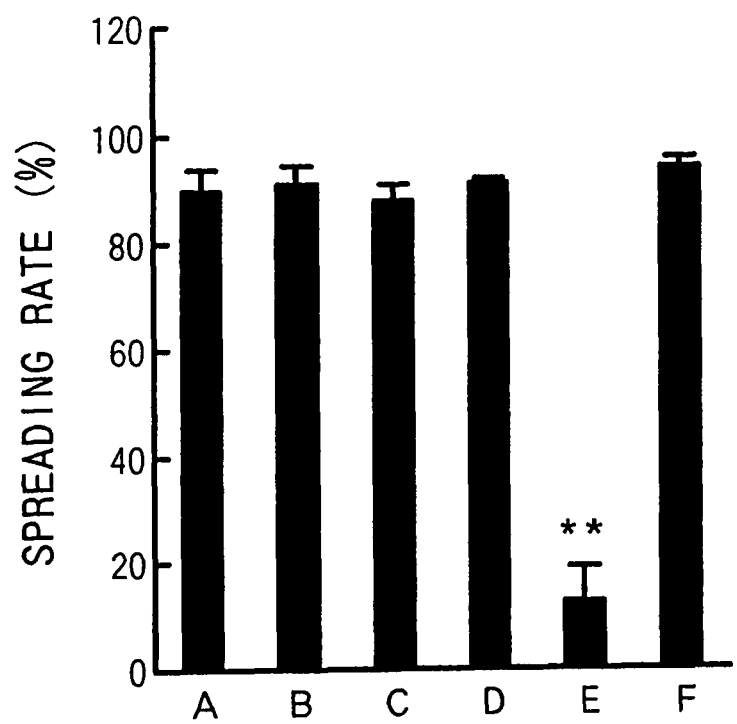
FIG. 4 is a graph of the spreading rates of melanoma cells which were cultured in the PBS (A), fibrinogen (B), batroxobin (C), thrombin (D), Des A fibrin (E) and fibrin (F)-treated wells.

Photomicrographs (45 magnification) of the melanoma cells cultured for 2 hours in each different treated well, are shown in FIG. 3. The spreading rates of the melanoma cells cultured in each different treated well, is shown in FIG. 4. Most of the melanoma cells developed pseudopodia and did spread (FIG. 3) in the presence of PBS (A), fibrinogen (B), batroxobin (C), thrombin (D) and fibrin (F), with a spreading rate over 80% in each case (FIG. 4).

On the other hand, in the presence of Des A fibrin (E), most of the treated melanoma cells remained round, and even if it took out the pseudopodium, their length was shorter than that in other above-mentioned cases (FIG. 3). The spreading rate of Treatment E is 12.53±6.69% (FIG. 4).

It is therefore shown that more than other factors, Des A fibrin significantly inhibits the spreading of melanoma cells in the presence of Matrigel (FIG. 4, p<0.01).

As mentioned above, it can be understood that Des A fibrin effectively suppresses spreading of melanoma cells.

(4) Inhibition of Breast Cancer Cell Spreading

Figure 5:
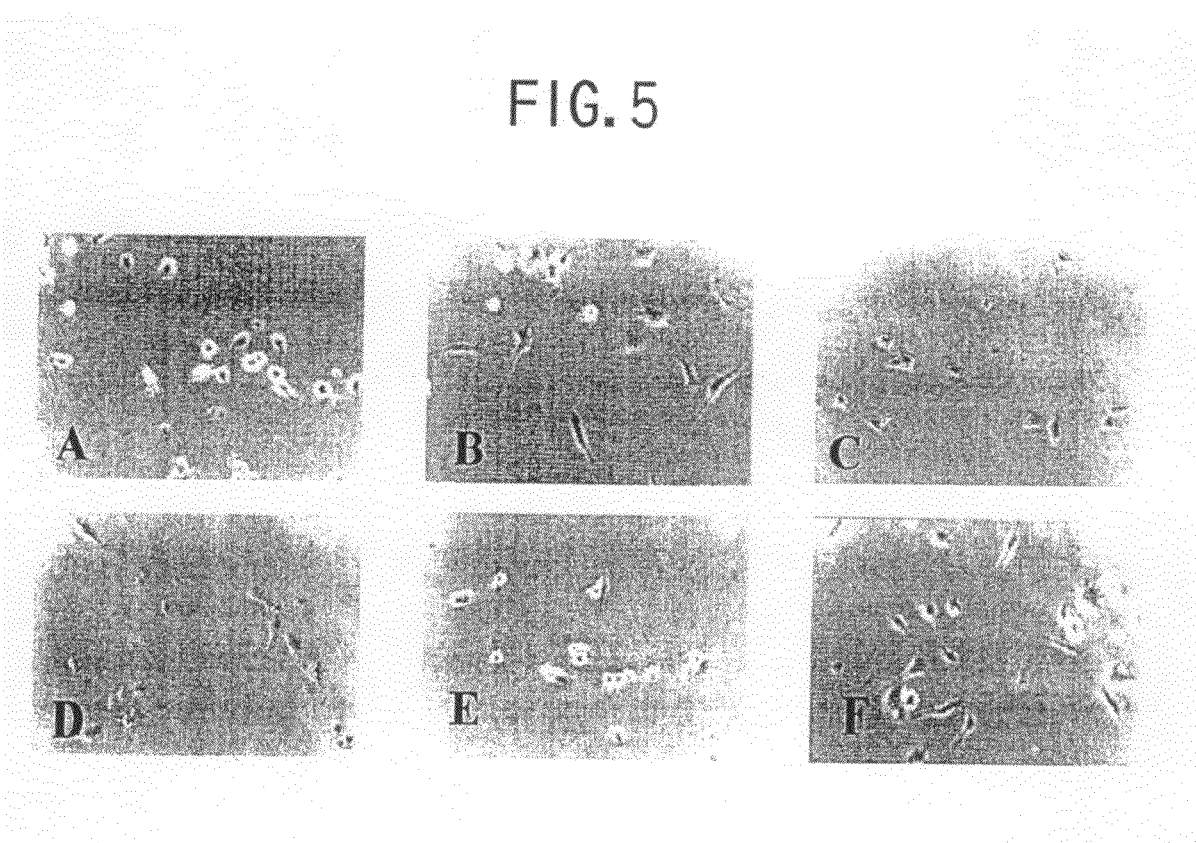
FIG. 5 shows photomicrographs of breast cancer cells which were cultured in the PBS (A), fibrinogen (B), batroxobin (C), thrombin (D), Des A fibrin (E) and fibrin (F)-treated wells.
Figure 6:
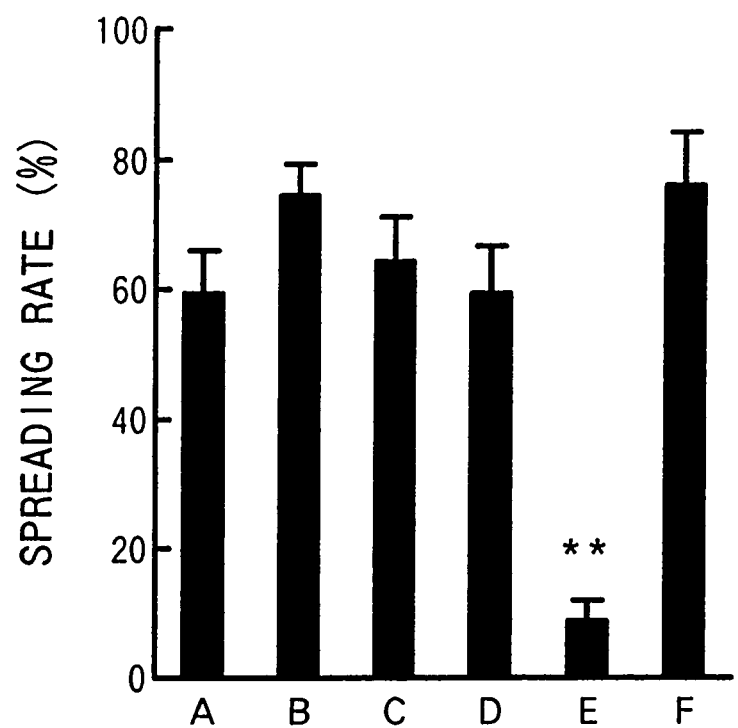
FIG. 6 is a graph of the spreading rates of breast cancer cells which were cultured in the PBS (A), fibrinogen (B), batroxobin (C), thrombin (D), Des A fibrin (E) and fibrin (F)-treated wells.

Photomicrographs (45 magnification) of the breast cancer cells cultured for 2 hours in each different treated well, are shown in FIG. 5. The spreading rates of the breast cancer cells cultured in each different treated well, is shown in FIG. 6. Most of the breast cancer cells developed pseudopodia and did spread (FIG. 5) in the presence of PBS (A), fibrinogen (B), batroxobin (C), thrombin (D) and fibrin (F), with a spreading rate over 60% in each case (FIG. 6).

On the other hand, in the presence of Des A fibrin (E), most of the treated breast cancer cells remained round, and even if it took out the pseudopodium, their length was shorter than that in other above-mentioned cases (FIG. 5). The spreading rate of Treatment E is 8.87±3.06% (FIG. 6).

It is therefore shown that more than other factors, Des A fibrin significantly inhibits the spreading of breast cancer cells in the presence of Matrigel (FIG. 6, p<0.01).

As mentioned above, it can be understood that Des A fibrin effectively suppresses spreading of breast cancer cells.

(5) Inhibition of Fibrosarcoma Cell Spreading

Figure 7:
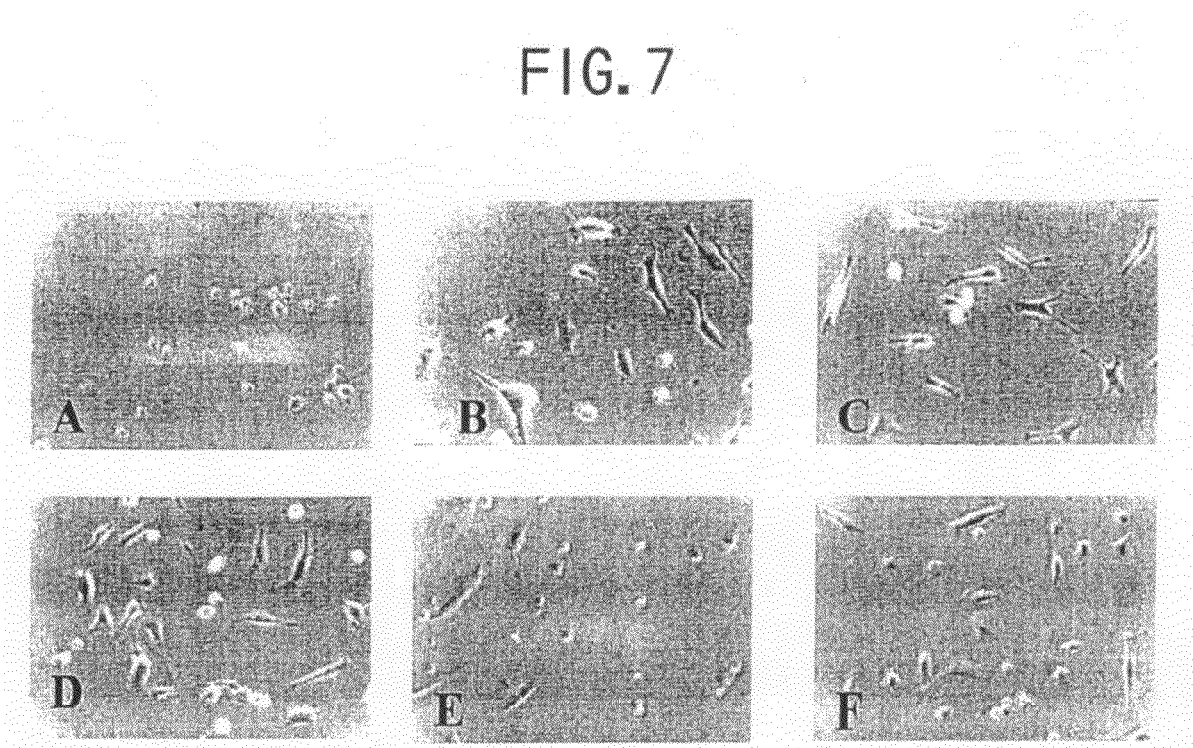
FIG. 7 shows photomicrograph of fibrosarcoma cells which were cultured in the PBS (A), fibrinogen (B), batroxobin (C), thrombin (D), Des A fibrin (E) and fibrin (F)-treated wells.
Figure 8:
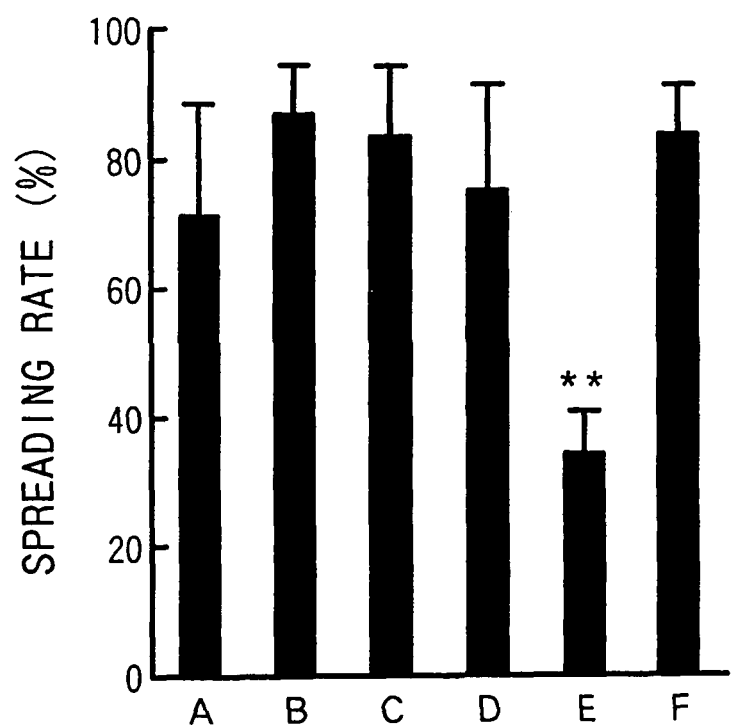
FIG. 8 is a graph of the spreading rates of fibrosarcoma cells which were cultured in the PBS (A), fibrinogen (B), batroxobin (C), thrombin (D), Des A fibrin (E) and (F) fibrin-treated wells.

Photomicrographs (45 magnification) of fibrosarcoma cells cultured for 2 hours in each different treated well, are shown in FIG. 7. The spreading rates of the fibrosarcoma cells cultured in each different treated well, is shown in FIG. 8. Most of the fibrosarcoma cells developed pseudopodia and spread (FIG. 7) in the presence of PBS (A), fibrinogen (B), batroxobin (C), thrombin (D) and fibrin (F), with a spreading rate over 70% in each case (FIG. 8).

On the other hand, in the presence of Des A fibrin (E), most of the treated fibrosarcoma cells remained round, and even if it took out the pseudopodium, their length was shorter than that in other above-mentioned cases (FIG. 7). The spreading rate of Treatment E is 34.19±6.55% (FIG. 8).

It is therefore shown that more than other factors, Des A fibrin significantly inhibits the spreading of fibrosarcoma cells in the presence of Matrigel (FIG. 7, p<0.01).

As mentioned above, it can be understood that Des A fibrin effectively suppresses spreading of fibrosarcoma cells.

Example 3

Effect of the Amount of Des A Fibrin on the Spreading of Malignant Tumor Cells

Figure 9:
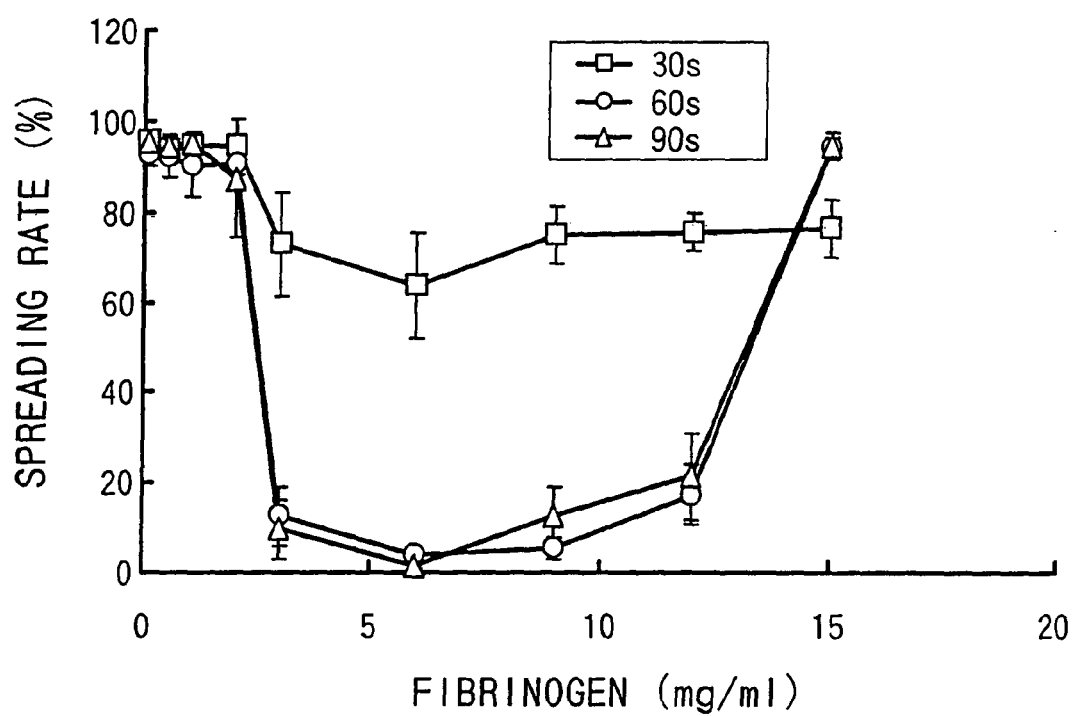
FIG. 9 is a graph showing the effect of Des A fibrin amounts on spreading of melanoma cells.

The amount of Des A fibrin produced by the action of batroxobin on fibrinogen is thought to increase as the amount of fibrinogen increases and as the reaction time between fibrinogen and batroxobin increases. Therefore, various amounts of Des A fibrin were prepared by reacting the same concentration of batroxobin (0.5 BU/ml) with differing concentrations of fibrinogen (0.1 mg/ml, 0.5 mg/ml, 1 mg/ml, 2 mg/ml, 3 mg/ml, 6 mg/ml, 9 mg/ml, 12 mg/ml and 15 mg/ml) for 30 seconds, 60 seconds and 90 seconds, respectively. The effects of which, on spreading of malignant tumor cells, were investigated. The experimental methods were similar to the Treatment E as mentioned in (2) The method of measuring cell spreading of Example 2 excluding the fibrinogen concentrations and reaction times. The results are shown in FIG. 9.

When the reaction time was 30 seconds (□), increasing the fibrinogen concentration did not affect the reduction of spreading rate, and the lowest spreading rate achieved was 76.23%. This is attributed to the fact that a sufficient amount of Des A fibrin to affect cell spreading, was not produced within a reaction time of 30 seconds.

When the reaction time was 60 seconds (O) and 90 seconds (Δ), a large reduction in the spreading rate was observed when the fibrinogen concentration reached 3 mg/ml (60 seconds: 12.53%, 90 seconds: 9.13%). When the fibrinogen concentration was further increased, almost no spreading cells were observed. These indicate that spreading of malignant tumor cells is inhibited even more as the amount of produced Des A fibrin increased.

On the other hand, when the fibrinogen concentration exceeded 9 mg/ml, the cell spreading rate began increasing, and at a concentration of 15 mg/ml no reduction effect on the cell spreading rate was observed. This is attributed to the effect of the fibrinogen itself that because in the presence of high concentration of fibrinogen, a large amount of fibrinogen covers a well before the well can be coated with the resulting Des A fibrin (non well-coated Des A fibrin is washed away by the washing process).

As mentioned above, it can be understood that Des A fibrin dose-dependently inhibits the spreading of melanoma cells.

Example 4

Effect of Des A Fibrin on Migration of Malignant Tumor Cells

Migration of malignant tumor cells is a biological behavior that forms the basis for tumor metastasis. The migratory ability of the malignant tumor with high malignancy is also high. In the present example, the effect of Des A fibrin on the migration of two types of malignant tumors (melanoma and breast cancer) were evaluating using a scratch wound assay (see *Gynecol. Oncol.* 89:60-72 (2003)).

(1) Malignant Tumor Cells Used

B16-BL6 mouse malignant melanoma cells (Academy of Chinese Medical Sciences, Beijing, China) as the melanoma cells were subcultured in RPMI-1640 medium (Gibco, MD, USA) containing 10% fetal bovine serum (FBS, HyClone, Utah, USA), and the cells were used in the present experiment.

MMT060562 mouse breast cancer cells (ATCC, VA, USA) as the breast cancer cells were subcultured in MEM medium (Gibco, MD, USA) containing 10% FBS and 1% nonessential amino acids solution (Non-Essential Amino Acids Solution, Gibco, MD, USA), and the cells were used in the present experiment.

(2) Measurement of Cell Migration

A cover glass was laid on each well of 6-well plates (Corning, N.Y., USA), and $2.5 \times 10^4$ B16-BL6 melanoma cells suspended in 2 ml of 10% FBS-containing RPMI-1640 medium or $2.5 \times 10^4$ MMT060562 breast cancer cells suspended in 2 ml of 10% FBS-containing MEM medium were seeded into the well and cultured for 24 hours in a $CO_2$ incubator.

After culture, a plastic cell scraper was used to make a 0.5 mm scratch line in the cover glass on which the cells had proliferated. The cells that had originally proliferated in the scratch line were removed, and the remaining cell fragments were washed in PBS.

Two milliliter of 0.05 mg/ml fibrinogen diluted with 10% FBS-containing RPMI-1640 medium or Des A fibrin (produced by addition of 0.05 mg/ml fibrinogen and 2 BU/ml batroxobin) was added to the melanoma cultured wells, and it was incubated for 48 hours in a $CO_2$ incubator.

Two milliliter of 0.05 mg/ml fibrinogen diluted with 10% FBS MEM or Des A fibrin (produced by addition of 0.05 mg/ml fibrinogen and 2 BU/ml batroxobin) was added to the breast cancer cultured wells, and it was incubated for 48 hours in a $CO_2$ incubator.

After being cultured, the Wright stained test is conducted, and the number of migrated cells to the scratch line were counted using a phase contrast microscope (Olympus, Tokyo, Japan) and represented as number of migrated cells per square millimeter of cover glass (number of cells/mm$^2$).

Further, because fibrinogen is present around the malignant tumor cells in vivo, fibrinogen treatment was used as the control of Des A fibrin treatment.

(3) Inhibition of Melanoma Cell Migration

The results are shown in Table 1.

TABLE 1

| Migration of melanoma cells | |
|---|---|
| Treatment | Number of migrated cells (cells/mm$^2$) |
| Fibrinogen | 87 ± 14 |
| Des A fibrin | 14 ± 4** |

**p < 0.01, compared with fibrinogen

When treated with Des A fibrin, the number of migrated cells (14±4 cells/mm$^2$) was significantly less than the number of migrated cells treated with fibrinogen (87±14 cells/mm$^2$) (p<0.01).

As mentioned above, it can be understood that Des A fibrin effectively inhibits the migration of melanoma cells.

(4) Inhibition of Breast Cancer Cell Migration

The results are shown in Table 2.

TABLE 2

| Migration of breast cancer cells | |
|---|---|
| Treatment | Number of migrated cells (cells/mm$^2$) |
| Fibrinogen | 29 ± 10 |
| Des A fibrin | 12 ± 3** |

**p < 0.01, compared with fibrinogen

When treated with Des A fibrin treatment, the number of migrated cells (12±3 cells/mm$^2$) was significantly less than the number of migrated cells treated with fibrinogen (29±10 cells/mm$^2$) (p<0.01).

As mentioned above, it can be understood that Des A fibrin effectively inhibits the migration of breast cancer cells.

INDUSTRIAL APPLICABILITY

As shown in the examples mentioned above, the malignant tumor-inhibiting preparation of the present invention can effectively inhibit the spreading and migration of malignant tumor cells. Therefore, the present invention can be advantageously used to inhibit malignant tumors.

The invention claimed is:

1. A method of inhibiting the growth, invasion and metastasis of a malignant tumor in a patient comprising the step of administering an effective amount of Des A fibrin to the patient wherein the malignant tumor is selected from the group consisting of melanoma, breast cancer and fibrosarcoma.

2. The method according to claim 1, wherein the Des A fibrin is obtained by the action of batroxobin on fibrinogen.

3. The method according to claim 2, wherein the batroxobin comprises a naturally occurring preparation or the products of genetic recombination.

* * * * *